July 22, 1975 TAKESHI YOICHI YONEMOTO Plant Pat. 3,747
CARNATION PLANT
Filed July 3, 1974
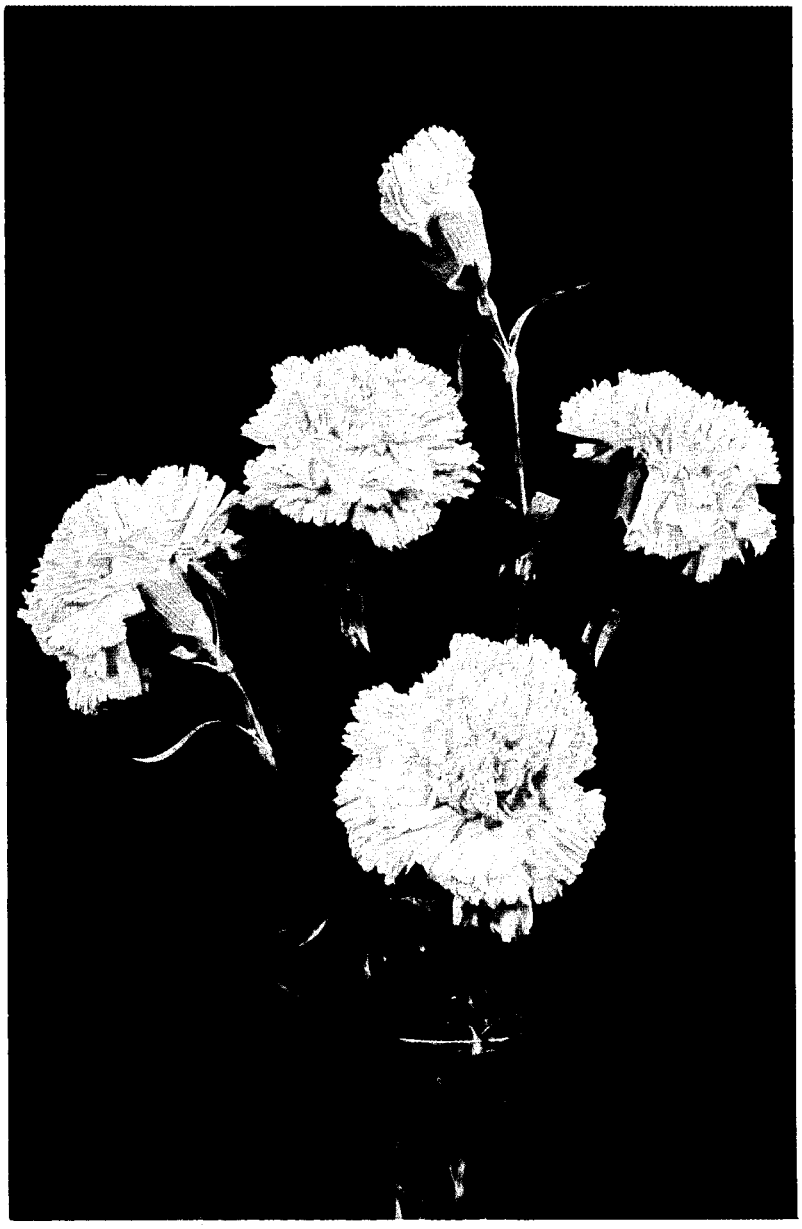

United States Patent

Plant Pat. 3,747
Patented July 22, 1975

3,747

CARNATION PLANT

Takeshi Yoichi Yonemoto, 1328 Henderson Ave., Santa Clara, Calif. 95051

Filed July 3, 1974, Ser. No. 485,385
Int. Cl. A01h *5/00*
U.S. Cl. Plt.—70 1 Claim

ABSTRACT OF THE DISCLOSURE

A new variety of carnation plant of the greenhouse type for cut flower production characterized by its profuse and continuous blooming habit and the light pink coloring of its medium-large blossoms which have occasional petals blotched or washed with white.

*Background of the New Plant*

This new carnation variety was discovered by me in 1969 at Santa Clara, Calif., as a sport of the variety Flamingo (unpatented) being grown in my greenhouse for the production of cut flowers. This sport caught my attention because of its gentle pink coloring whereas the flowers of the parent, Flamingo, are of a dark salmon pink color and in an entirely different color category than this sport.

Asexual reproduction of this sport was done by me by means of cuttings in my greenhouse at Santa Clara, Calif., and continued propagation of this new variety by cuttings and under my direction through many generations has demonstrated that the new coloring of the plant is firmly fixed and holds true from generation to generation.

*Description of the Drawing*

My new variety of carnation plant is illustrated by the accompanying drawing which shows buds and blossoms of the plant in full color which is reproduced as faithfully as possible through the use of conventional photographic procedures.

*Description of the New Plant*

The following is a detailed description of my new variety of carnation plant with color designations according to the R.H.S. Colour Chart of The Royal Horticultral Society at London, England.

THE PLANT

Origin: Sport.
Parentage: Flamingo (unpatented).
Classification:
- Botanic—*Dianthus caryophyllus.*
- Commercial—Greenhouse carnation for cut flowers.

Form: Bush.
Height: Regular for Sim varieties.
Growth: Vigorous, strong and upright.
Foliage: Quantity—average, 10 leaves per stem.
- Size: Regular.
- Shape: Gently or moderately curled and lanceolate in form with entire margin.
- Color: Green.
- Texture: Smooth.
- Ribs: Single, along center of leaf.
- Petioles: None. The leaf is decurrent and amplexicaul.

THE BUD

Size: Medium.
- Diameter—About ¾ inches.
- Length—1½ inches, when bud is about to open.

Form: Long ovoid with pointed tip.
Opening Rate: Six days.
Color: When pentals begin to unfurl:
- Outside—Dark pink.
- Inside—Light pink.

Sepals: Long oval with rounded tip. Sepals stand up but curl back slightly at tips.
- Color: Pale green.

Calyx: Pear shaped.
- Aspect: Smooth.
- Tendency to Split: About 5%.

Peduncle (Stem): Up to 24 inches in length.

THE FLOWER

Blooming Characteristics: Continuous and profusely blooming.
Size of Bloom: Medium.
- Diameter—3 inches.
- Depth—1½ inches.

Shape: Cup shaped at first opening, becoming flatter and more open as blossom matures.
Borne: Singly.
Petalage: Number of petals—65 to 70 in more or less imbricated arrangement.
- Form: Fan shaped with deeply serrated or frilled undulating margins.
- Color: Outer petal body—Deep pink R.H.S. 51C. Inner petal body—Lighter pink R.H.S. 50D. Reverse side—Lighter pink than inner petal body.
- Appearance: Satiny.
- Texture: Soft.

Fragrance: Typical carnation.
Lasting Quality:
- On plant—10 days.
- As cut flower—10 days.

REPRODUCTIVE ORGANS

Stamens:
- Anthers: Arrangement—Filaments emerge from base of ovary and anthers are rudimentary.
- Filaments: ⅝ inch long and white in color.
- Pollen: None.

Pistils:
- Styles: ⅝ inch long.
- Stigmas: Light pink in color.

Ovaries: Oblong in shape, 7/10 inch high x 5/16 wide at middle. Green in color.

I claim:

1. A new and distinct variety of carnation plant, substantially as herein shown and described, characterized by the light pink coloring of its blooms which are of medium size and which have many outwardly projecting guard petals splotched with white at their outer ends, and by its profuse and continuous production of blossoms when grown in greenhouse for cut flowers.

No references cited.

ROBERT E. BAGWILL, Primary Examiner